United States Patent [19]
Brisendine

[11] Patent Number: 5,634,792
[45] Date of Patent: Jun. 3, 1997

[54] DENTURE REPAIR KIT

[76] Inventor: Frank R. C. Brisendine, P.O. Box 9188, Helena, Mont. 59604

[21] Appl. No.: 271,005

[22] Filed: Jul. 5, 1994

Related U.S. Application Data

[63] Continuation of Ser. No. 46,767, Apr. 12, 1993, abandoned.
[51] Int. Cl.$^6$ ................................................. A61C 13/225
[52] U.S. Cl. ..................... 433/180; 433/142; 433/167; 433/181
[58] Field of Search ....................... 433/141, 142, 433/144, 148, 149, 167, 171, 180, 181, 199.1, 229

[56] References Cited

U.S. PATENT DOCUMENTS

| | | | |
|---|---|---|---|
| 3,644,996 | 2/1972 | Weinkle | 433/171 |
| 3,846,911 | 11/1974 | Wichner | 433/171 |
| 4,274,826 | 6/1981 | Huey et al. | 433/142 |
| 4,364,473 | 12/1982 | Bogaert et al. | 433/229 |
| 4,470,815 | 9/1984 | Hazar | 433/171 |
| 4,634,561 | 1/1987 | DeLuca | 433/171 |
| 5,242,304 | 9/1993 | Truax et al. | 433/181 |

*Primary Examiner*—Christopher A. Bennett
*Attorney, Agent, or Firm*—George R. McGuire

[57] ABSTRACT

A kit whose contents permit a denture wearer to repair their own dentures. The kit contains replacement teeth, a liquid monomer and a powdered polymer which when added together form a putty-like acrylic, a pipette for dispensing the liquid, a specially designed grinding and filing tool, a piece of emery paper, and a strip of wax used for temporarily bridging a loose tooth to a fixed tooth. Instructions explaining a method for repairing both simple and complex denture fractures, as well as replacing broken or lost denture teeth are also included in the kit. The methods each utilize the specially designed grinding and filing tool.

7 Claims, 3 Drawing Sheets

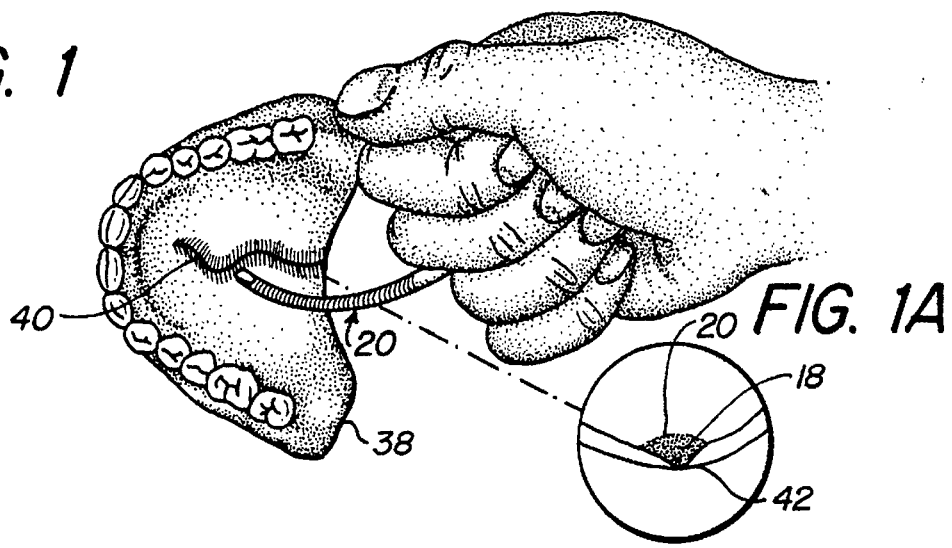
FIG. 1
FIG. 1A
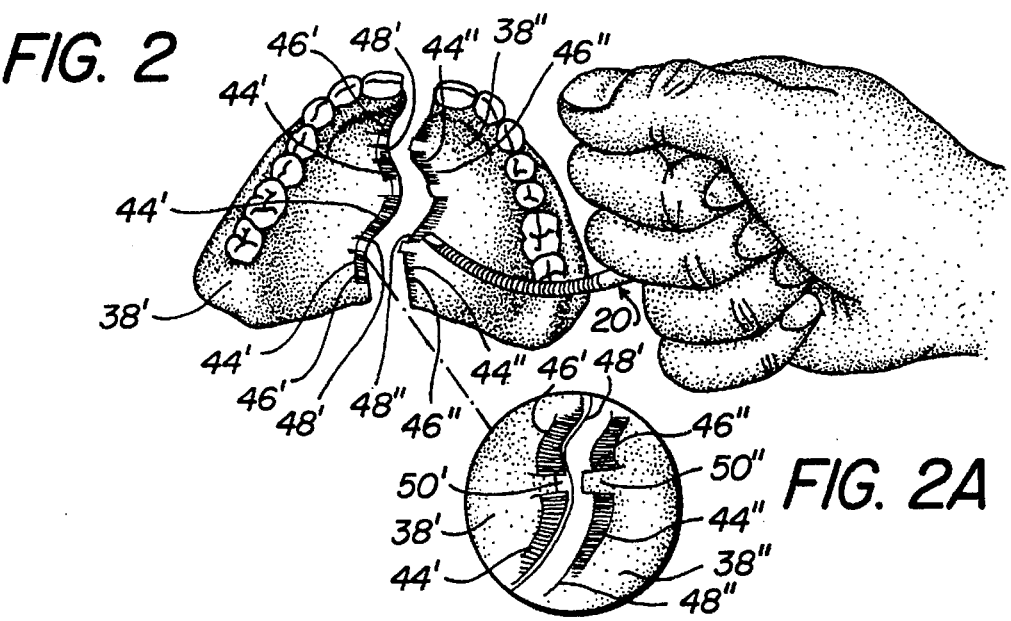
FIG. 2
FIG. 2A
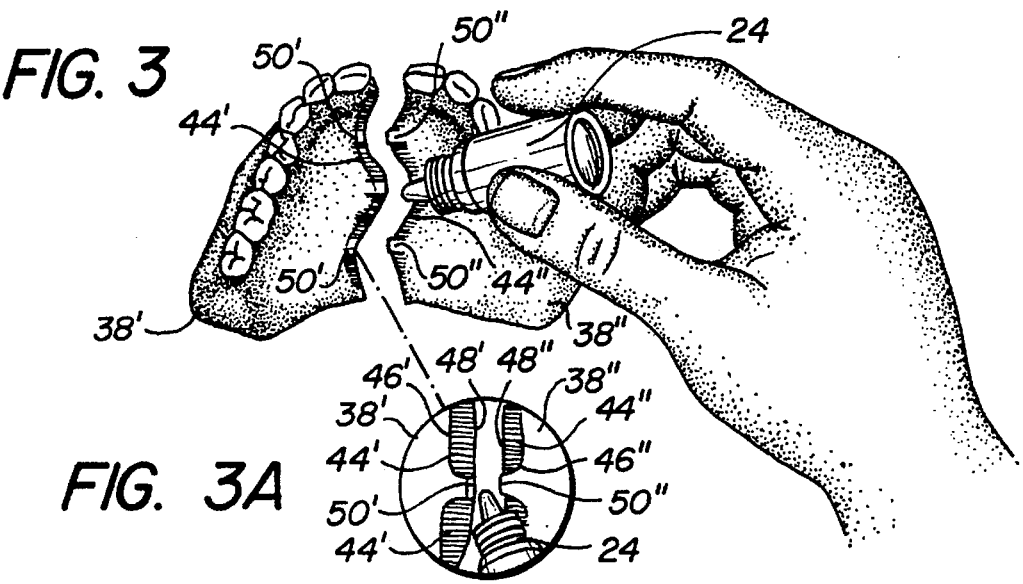
FIG. 3
FIG. 3A

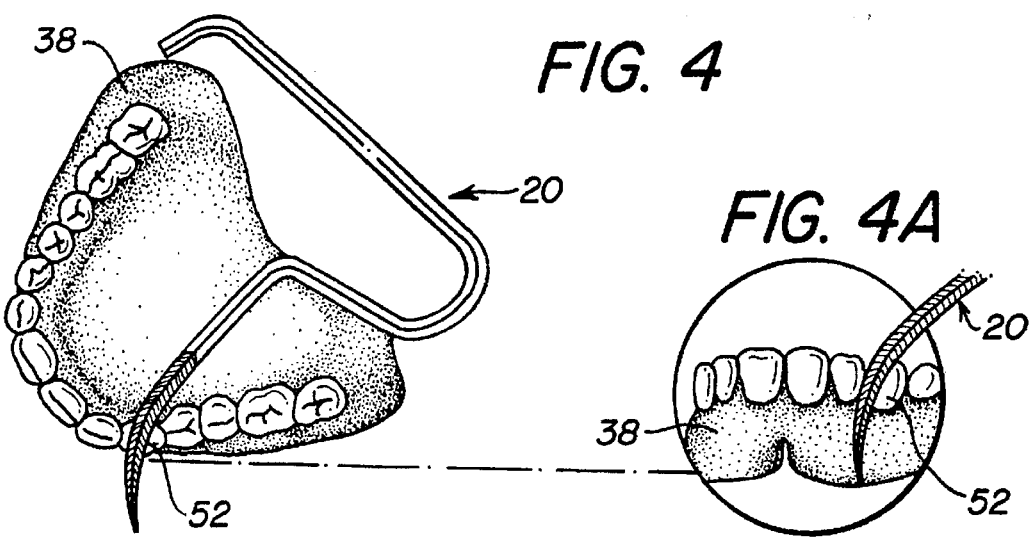
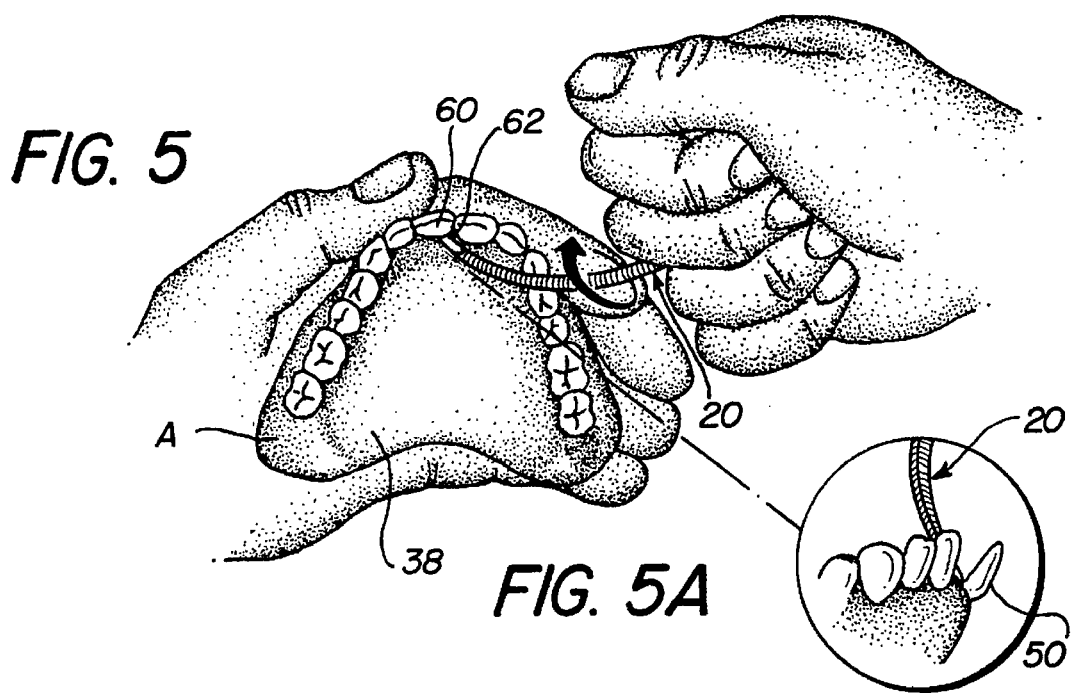
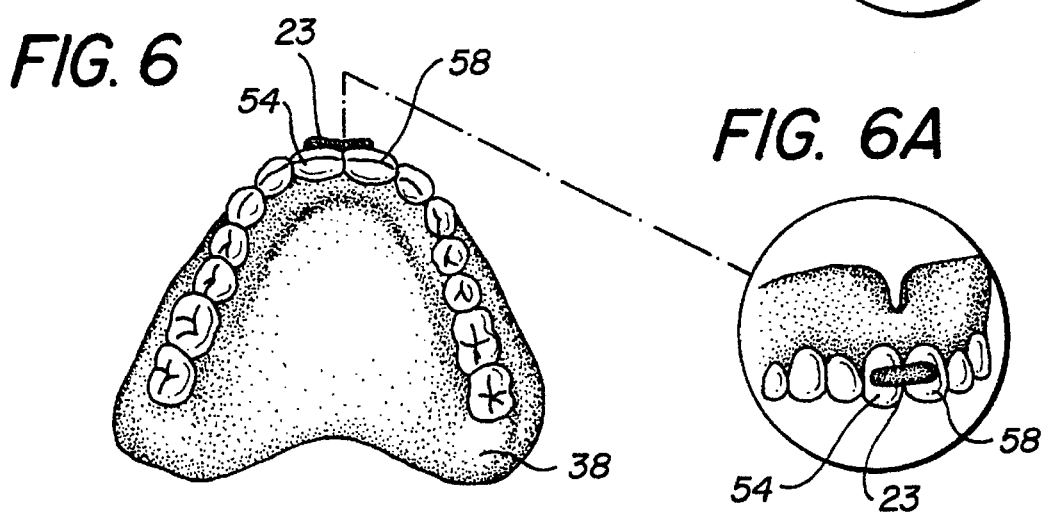

5,634,792

DENTURE REPAIR KIT

REFERENCE TO RELATED APPLICATION

This application is a continuation of U.S. patent application Ser. No. 08/046,767, filed Apr. 12, 1993, now abandoned.

BACKGROUND OF THE INVENTION

1. Field of Invention

The present invention relates generally to dental prosthesis, and more particularly to a new and improved kit for self-repair of dental prosthesis and a method of using the kit.

2. Introduction

Traditionally when a denture became fractured or a tooth from a denture broke or fell out, it was necessary to bring the broken denture to a professional dental technician to have it repaired. Not only was this inconvenient for a denture wearer since the denture was useless until it was repaired, but it could also be detrimental to a denture wearer's health or career since solid foods could not be chewed and words could not be understandably spoken. Furthermore, if the denture were to break while on vacation, either a technician would have to be found in that particular location or the denture would simply have to wait to be repaired until the vacation was ended. In either case, the vacation is far less enjoyable than if the denture had not broken.

Eventually some denture self-repair kits were developed. These kits permitted fractured dentures to be temporarily repaired, but did not provide enough tools or instructions to permanently repair the denture. Furthermore, using prior art denture repair left bumps and cracks in the denture which would interfere with the wearer's tongue and speech. In addition, none of the prior art kits provide any means for replacing a broken or lost denture tooth, thus if a tooth broke it would still be necessary to resort back to a dental technician to have the denture repaired.

A self-repair denture kit having the features described above is exemplified in U.S. Pat. No. 4,270,904 issued to Bogaert on Jun. 2, 1981. The '904 patent essentially discloses a kit having a fast-setting adhesive having an affinity for the denture material, and separate containers of a liquid monomer and a powdered polymer which, when mixed together, form a hard acrylic.

The method set forth in the '904 patent simply attempts to weld a fractured denture back together without removing any of the existing acrylic around the fracture. Therefore the repair is somewhat weak and easily susceptible to another fracture. Further, the repair is messy and lumpy thus causing uncomfortable, irritable feelings with the tongue. Also, the '904 patent offers no tools or methods for repairing a lost or broken denture tooth.

OBJECTS AND ADVANTAGES

It is therefore a principal object of the present invention to provide a kit for self-repairing dentures having means for replacing broken or lost denture teeth.

It is another object of the present invention to provide denture repair kit which utilizes a method that will repair a broken denture back to its original strength.

It is a further object of the present invention to provide a denture repair kit having a new and improved grinding tool that may be easily used by a layman.

It is yet another object of the present invention to provide a denture repair kit which is both inexpensive and simple to manufacture.

Other objects will in part be obvious and in part appear hereinafter.

SUMMARY OF THE INVENTION

In accordance with the foregoing objects and advantages, the present invention is generally comprised of a self-repair denture kit having both denture fracture repair elements and denture replacement teeth contained therein. In addition, new and improved methods of repairing dentures in accordance with the kit of the present invention is also disclosed herein.

The contents of the denture repair kit include a plurality of both upper and lower anterior replacement teeth, a bottle of a liquid monomer (i.e., methyl-methacrylate), a bottle of powdered polymer (i.e., also methyl-methacylate), a grinding and filing tool, a pipette for dispensing the liquid monomer, a piece of emery paper, a strip of wax, and a bottle or tube of fast-setting adhesive. Each of the contents of the kit with the exception of the grinding tool are conventional to the art, but they have never been compiled together into a kit for use by a denture wearer since no methods have been developed which are simple enough for any layperson to perform the denture repair.

The grinding tool includes a handle portion which permits it to be easily manipulated by anyone, a file portion which enables it to grind away superfluous acrylic from the denture, and a pointed distal end which permits it to dig into a denture and remove teeth. The tool is used in the methods for repairing both simple and compound fractures and in the methods for replacing either plastic or porcelain artificial teeth.

The methods for repairing both simple and compound fractures include several common steps. First, a V-shaped groove needs to be etched into the denture along the fracture line. Next, powdered polymer is dispensed into the groove until the groove is full. Liquid monomer is then dispensed onto the powder. This mixture forms a putty which hardens over a short period of time and forms a strong weld along the fracture line. Additional liquid monomer may be added to the mixture and spread evenly over the fracture to smooth out the repair. The denture can then be placed in warm water for a predetermined period of time. The roughness of the repair may then be sanded using emery paper and then polished using toothpaste. Although there are a few other steps involved in repairing a compound fracture, the above-described process is the essence of the repair.

To remove and replace a broken plastic tooth it is necessary to first file the remaining portions of the broken tooth away. An appropriately sized tooth can then be chosen from the teeth supplied in the kit. Any rough corners of the tooth can be filed to get a more cooperatively shaped tooth. Once inserted into the empty space a strip of wax can be bridged between the new tooth and its adjacent tooth, thereby holding it in place. The powdered polymer and liquid monomer can then be added in the voids surrounding the new tooth. The denture can then be submerged in warm water for a predetermined period of time. Once the repair has hardened, it may be sanded and polished, thus putting the denture back to its original condition.

To remove a porcelain tooth, the pointed end of the filing tool is used to drill a hole about 4 mm deep directly behind the broken tooth. The tool can then be inserted into the hole and pried upwardly and outwardly against the tooth until the tooth becomes removed from the denture. The steps of replacing the old tooth with a new tooth are the same as previously described for the plastic tooth.

The present invention will be described in greater detail hereinafter.

BRIEF DESCRIPTION OF THE DRAWINGS

The present invention will be further described in connection with the accompanying drawings, in which:

FIG. 1 is a top plan view of an upper denture having a simple fracture;

FIG. 1a is an enlarged end view of a portion of the fracture shown in FIG. 1;

FIG. 2 is a top plan view of an upper denture having a compound fracture;

FIG. 2a is an enlarged top view of a portion of the denture of FIG. 2 showing in detail the abutment areas thereof;

FIG. 3 is the top plan view of FIG. 2 and further showing quick setting glue being applied to the denture;

FIG. 3a is an enlarged top view of the portion of the denture having the glue applied thereto;

FIG. 4 is a top plan view of an upper denture having a broken tooth and further showing the placement of a tool used to remove the broken tooth;

FIG. 4a is an enlarged end view of FIG. 4 showing, in particular, the positional relationship between the tool and the broken tooth;

FIG. 5 is a top plan view of an upper denture and tooth removal tool showing, with a directional arrow, how to utilize the tool to remove a tooth;

FIG. 5a is an enlarged side view of FIG. 5 showing the tooth being removed with the tool;

FIG. 6 is a top plan view of an upper denture having a new tooth held in place by a strip of wax;

FIG. 6a is an enlarged front view of FIG. 6 showing the new tooth being held by the strip of wax.

DETAILED DESCRIPTION

Figure 7:
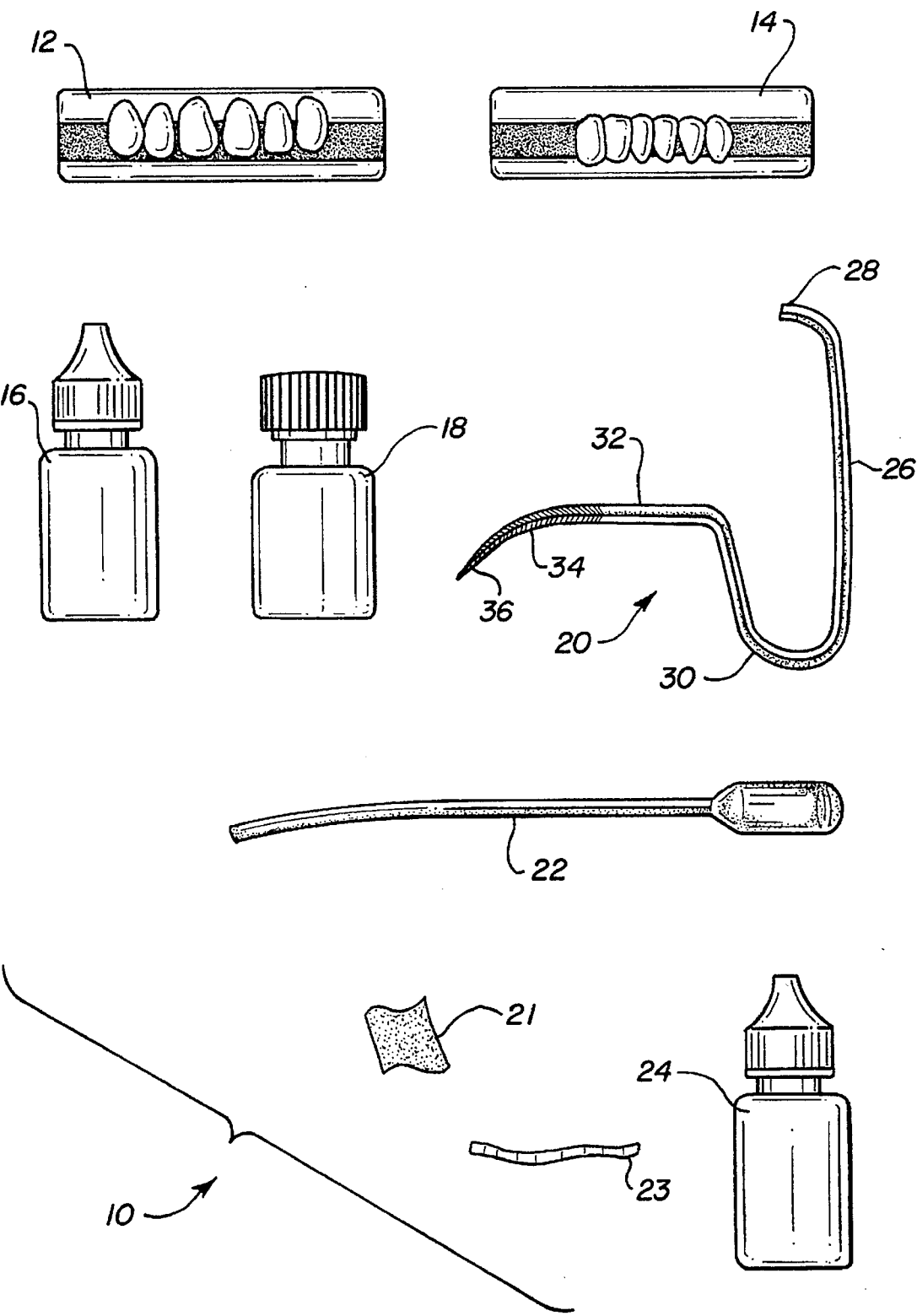
FIG. 7 is a front elevational view of the contents contained in a denture repair kit.

Referring now to the drawing figures wherein like reference numerals refer to like parts throughout, there is seen in FIG. 7 the contents of a denture repair kit, denoted generally and collectively by reference numeral 10, intended to be used by a denture wearer whose denture has been fractured to some extent or who has lost or broken at least one of the false teeth. Kit 10 includes a set of upper anterior replacement teeth 12, a set of lower anterior replacement teeth 14, a bottle of a liquid monomer 16 (preferably methyl-methacrylate), a bottle of a powdered polymer 18 (also preferably methyl-methacrylate), a specially designed grinding and tooth removal tool 20, a small sheet of emery paper 21, a pipette 22 used for dispensing monomer 16, a strip of wax 23 and a bottle of quick setting glue 24. By providing all of the above identified elements, essentially any individual can, by properly following written instructions also provided with the kit or its packaging, repair a broken denture or replace a lost or broken tooth from a denture.

While replacement teeth 12 and 14, monomer 16, polymer 18, pipette 22 and glue 24 are all commercially available, grinding tool 20 is specially designed to provide a mechanism for a layperson to accurately and effectively repair a broken denture. Furthermore, since no mechanisms have existed which permit a broken or lost denture tooth to be repaired by a layperson, replacement teeth, such as teeth 12 and 14, have never been of any use to the layperson and thus have been unavailable to them.

Grinding tool 20 includes a handle portion 26 which extends between a first end portion 28 and an intermediate, curved portion 30. Handle portion 26 is adapted to comfortably receive index and middle fingers, and end 28 angles downwardly from handle portion 26 to permit a thumb to comfortably rest thereon, as is clearly seen in FIGS. 1 and 5. Curved portion 30 extends from handle portion 26 back towards first end portion 28 and angularly away from handle portion 26 to ensure enough space for fingers to wrap around handle portion 26. Shank portion 32 extends from curved portion 30 substantially perpendicularly with respect to handle portion 26. Filing portion 34 extends from a second end portion 36 to an intermediate point on shank portion 32. Second end portion 36 tapers to a point and is curved with respect to shank portion 32. As shown, tool 20 is formed from a length of stock having a square or triangular cross section to provide a more effective grinding and tooth removal tool, as appears hereinafter.

Referring now to FIGS. 1 and 1a there is seen an upper denture 38 having a simple mid-line fracture 40. To repair the simple fracture using the contents of the kit previously described, first a V-shaped notch 42 (FIG. 1a) is carved into the lingual surface of the denture on each side of fracture 40 using filing portion 34 of tool 20. The square or triangular cross section of tool 20 assists in forming notch 42 in a V-shape. Notch 42 is then filled flush (or slightly overfilled) with powdered polymer 18 as is seen in FIG. 1a. Next, using pipette 22, liquid monomer 16 is placed on powdered polymer 18 until polymer 18 becomes sufficiently damp. If filling small sections of notch 42 at one time, this process is repeated until the entire notch 42 is filled with polymer 18. Once the acrylic formed by the mixture of polymer 18 and monomer 16 becomes hard, additional monomer 16 is applied to the surface of the acrylic. The additional monomer 16 should be smoothed over the acrylic surface using either a finger or some spatula-like tool. Denture 38 is then placed into warm water to accelerate curing of the acrylic for about 10 minutes or until the acrylic has sufficiently hardened. Fine emery paper 21 may then be used to remove any rough portions of the repair and produce a smooth, flat surface which is flush with denture 38 and comfortable to the wearer. The repair may then be completed by polishing entire denture 38 with toothpaste, thus removing any loose grit which may be present after sanding the repair.

Referring now to FIGS. 2, 2a, 3 and 3a, there is seen two portions 38' and 38" of a completely fractured denture. To repair a compound fracture using the kit of this invention, it is first necessary to piece denture halves 38' and 38" back together by hand and check for any voids or missing pieces. If there are no voids or missing pieces to the denture, the repair can begin to be made.

To begin repair of the fractured denture, the lingual surfaces of both portions 38', 38" are ground away by filing portion 34 of tool 20 in several spaced areas 44', 44" adjoining the fracture line. Areas 44', 44", after grinding, extend from the lingual surface of the denture portions to the fracture line. Thus, when portions 38', 38" are placed with their respective fracture lines or edges in mating engagement, a plurality of spaced, V-shaped notches (each essentially the same as notch 42 of FIG. 1a) are provided along the fracture line, separated by an unground, abutment area 50', 50".

Following such grinding, a small quantity of glue 24 is applied to opposing surfaces of abutment areas 50', 50", as shown in FIG. 3. Portions 38', 38" are then placed and held in mating relation until the glue sets sufficiently, following which each of the V-shaped grooves formed by opposing areas 44', 44" may be filled in the manner described in connection with FIGS. 1 and 1a.

Referring now to FIGS. 4, 4a and 6, 6a there is seen a denture 38 having a broken plastic tooth 52. Broken tooth 52 may be removed and replaced with a new tooth 54 by following the procedure explained hereinafter.

First, using the filing portion 34 of tool 20, plastic tooth 52 may be completely filed away as is clearly seen in FIG. 4a. Once tooth 52 is removed, an appropriate new replacement tooth 54 may be chosen from the teeth 12, 14 supplied with the kit. New tooth 54 may then be adjusted to fit the space left by tooth 52 by using emery paper 21 to sand away any awkwardly shaped portions. New tooth 54 may then be inserted into denture 38 and held in place by bridging a small strip of wax 23 across new tooth 54 and its adjacent tooth 58 as is shown in FIG. 6. Next, powdered polymer 18 is spread around the cavitated areas left by tooth 52 and not completely filled by tooth 54. Once powdered polymer 18 is dispensed, sufficient liquid monomer 16 is added to polymer 18 to dampen it. As the mixture (acrylic) begins to harden, additional monomer 16 may be added thereto. The additional monomer may then be smoothed around tooth 54. Denture 38 is then submerged in warm water for about 10 minutes or until the repair becomes sufficiently hard. After removing denture 38 from the water, the repaired area can be sanded using emery paper 21 and polished with toothpaste.

Referring now to FIGS. 5, 5a, 6, 6a there is seen a denture 38 having a broken porcelain tooth 60. The procedure set forth hereinafter explains how to remove porcelain tooth 60 and replace it with a new tooth 54 taken from the teeth 12, 14 supplied in the kit.

To remove porcelain tooth 60 it is necessary to first, gouge or drill a hole 62 about 4 mm deep into denture 38 in close proximity to and directly behind tooth 60. The drilling can be done using pointed end 36 of tool 20. Next, tooth 60 can be removed by placing end 36 of tool 20 into hole 62 and prying upwardly and outwardly (i.e., in the direction indicated by the directional arrow shown in FIG. 5) against tooth 60 until the tooth is removed. FIG. 5a clearly shows tooth 60 coming out of denture 38.

Once tooth 60 is removed, an appropriate tooth 54 can be chosen from the replacement teeth 12, 14. After tooth 54 is filed to cooperatively fit denture 38, it is placed in the space previously occupied by tooth 60. As before, a strip of wax 22 is bridged across tooth 54 and its adjacent tooth 58, and powdered polymer 18 is placed in the cavitated areas, including hole 62, left by tooth 60 and not filled by tooth 54. Liquid monomer 16 is then added to powder 18 until it is sufficiently dampened. After letting the mixture set for a moment additional liquid 16 may be added to the mixture and smoothed out using a finger or a spatula-like tool. Again the denture is then submerged in water for about 10 minutes or until the repair is sufficiently hard. The repaired area is then sanded using emery paper 21 and polished with toothpaste.

While specific materials and quantities were disclosed herein, the spirit and scope of this patent should not be limited thereto. Instead, the scope should extend to include all equivalents which fall within the claims as defined hereinafter.

What is claimed is:

1. A kit for performing self-repair of dental prosthesis having a plurality of original teeth, said kit comprising:

a) a package of a liquid monomer;

b) a package of a powdered polymer;

c) a plurality of replacement teeth of different shapes; and d) a grinding tool having proximal and curved, pointed distal end portions, a handle portion of predetermined length for comfortably receiving at least two fingers in wrapping relation therearound integrally extending, and angularly offset from said proximal end portion to an intermediate position, and a shaft portion extending substantially perpendicularly from said handle portion between said intermediate position and said distal end portion, at least a portion of said shaft portion having a filing surface.

2. The invention according to claim 1 and further comprising a pipette for dispensing said liquid monomer.

3. The invention according to claim 2 wherein both said liquid monomer and said powdered polymer are methylmethacrylate.

4. The invention according to claim 1 and further comprising at least one strip of wax adapted to bridge said at least one replacement tooth to an adjacent tooth contained in said dental prosthesis.

5. The invention according to claim 1 and further comprising a package of liquid adhesive.

6. The invention according to claim 1 and further comprising a tool having proximal and distal end portions with a manually engageable portion adjacent said proximal end portion.

7. The invention according to claim 1 wherein at least the portion of said tool having said filing surface is of square or triangular cross section.

\* \* \* \* \*